United States Patent
Doyle et al.

(10) Patent No.: US 9,329,147 B1
(45) Date of Patent: *May 3, 2016

(54) ELECTRONIC DATA SECURITY APPARATUS

(71) Applicant: International Business Machines Corporation, Armonk, NY (US)

(72) Inventors: Matthew S. Doyle, Syracuse, NY (US); Joseph Kuczynski, North Port, FL (US); Kevin A. Splittstoesser, Stewartville, MN (US); Timothy J. Tofil, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/578,737

(22) Filed: Dec. 22, 2014

(51) Int. Cl.
G06F 21/70 (2013.01)
G01N 27/04 (2006.01)
G06F 21/79 (2013.01)

(52) U.S. Cl.
CPC .............. *G01N 27/045* (2013.01); *G06F 21/79* (2013.01)

(58) Field of Classification Search
CPC ......... H01L 21/44; H01L 21/48; H01L 31/00; H01L 24/18; H01L 24/82; H01L 23/5389; H01L 27/14603; H01L 27/14609; H01L 27/14647; H01L 27/1641; H01L 31/036; H01L 31/1013; H01L 24/80; H01L 24/83; H01L 21/4857; H01L 2224/18; H01L 2924/01005; H01L 2924/01015; H01L 2924/01027; H01L 2924/01029; H01L 2924/01033; H01L 2924/01078; H01L 2924/01082; H01L 2924/14; H01L 2924/19041; H01L 2924/19042; H01L 2924/30105; H01L 2924/30107; H01L 2924/3025; H01L 2924/01006; H01L 2924/014; H01L 23/5225; H01L 23/576; H05K 1/185; H05K 3/4623; H05K 3/4652; H05K 2201/09509; H05K 2201/10636; H05K 2201/10674; G06F 21/87; G06K 19/073; H01Q 1/2208; H01Q 1/526; Y02P 70/611
USPC ...................... 726/34–36; 257/440, E21.509, 257/E23.131, E23.178; 250/208.1; 438/73, 438/80, 118
See application file for complete search history.

(56) References Cited

U.S. PATENT DOCUMENTS

| | | | |
|---|---|---|---|
| 5,030,796 | A | 7/1991 | Swanson et al. |
| 5,285,734 | A | 2/1994 | MacPherson |

(Continued)

OTHER PUBLICATIONS

Doyle et al., "Electronic Data Security Apparatus," U.S. Appl. No. 14/583,921, filed Dec. 29, 2014.

(Continued)

*Primary Examiner* — Thanhnga B Truong
(74) *Attorney, Agent, or Firm* — Nicholas D. Bowman; Robert Williams

(57) ABSTRACT

An apparatus for providing security for an integrated circuit (IC) chip is disclosed. The apparatus may include the IC chip, attached to a surface of a printed circuit board (PCB). The PCB may include a first, electrically insulative, conformal coating layer attached to the PCB surface and to exposed IC chip surfaces. The PCB may also include a Wheatstone bridge circuit to indicate changes to a second, X-ray opaque, optically opaque and electrically resistive, conformal coating layer. The circuit may include four resistors, formed from second conformal coating layer regions, four sets of electrically conductive pads on the PCB, each set electrically connected to a resistor of the four resistors. The circuit may also include a voltage source, connected to two conductive pads and a monitoring device, connected to another two conductive pads and configured to detect a change of resistance of the Wheatstone bridge.

7 Claims, 4 Drawing Sheets

(56) References Cited

U.S. PATENT DOCUMENTS

| | | | |
|---|---|---|---|
| 5,353,350 A | 10/1994 | Unsworth et al. | |
| 6,929,900 B2 | 8/2005 | Farquhar et al. | |
| 7,015,823 B1 | 3/2006 | Gillen et al. | |
| 7,282,394 B2 * | 10/2007 | Cho | H01L 24/18 257/E21.509 |
| 7,549,064 B2 | 6/2009 | Elbert et al. | |
| 7,710,286 B1 | 5/2010 | Thornley et al. | |
| 7,772,974 B2 | 8/2010 | Ehrensvard et al. | |
| 7,901,977 B1 | 3/2011 | Angelopoulos et al. | |
| 8,530,991 B2 * | 9/2013 | Tian | H01L 27/14603 250/208.1 |
| 8,530,992 B2 * | 9/2013 | Tian | H01L 27/14603 250/208.1 |
| 2001/0056542 A1 | 12/2001 | Cesana et al. | |
| 2009/0001821 A1 * | 1/2009 | Walker | G06F 21/87 307/413 |
| 2014/0143881 A1 | 5/2014 | Boday et al. | |

OTHER PUBLICATIONS

Kulkarni et al., "Processing and formulation of inkjet printable conducting polyaniline based ink for low cost, flexible humidity sensors using untreated polymeric substrate,"IOPscience, Smart Materials and Structures, Published Feb. 17, 2012, vol. 21, No. 3, © 2012 IOP Publishing Ltd.

Wikipedia, "Polyaniline," Wikipedia, The Free Encyclopedia, last modified Aug. 2, 2014, last accessed Sep. 19, 2014.

List of IBM Patents or Patent Applications Treated as Related, signed Dec. 29, 2014, 2 pgs.

\* cited by examiner

ELECTRONIC DATA SECURITY APPARATUS

BACKGROUND

The present disclosure generally relates to protecting sensitive electronic data. In particular, this disclosure relates to an apparatus designed to provide multiple levels of data protection for data stored within an integrated circuit (IC) chip.

The widespread use of computers and electronic systems, especially computers interconnected by networks such as the Internet, has caused data represented electronically to become ubiquitous. Electronic data may include a variety of file formats such as text, word processing documents, graphics data, still images, audio tracks and video data.

A wide range of information content, including "sensitive" information items may be represented electronically. Sensitive information may include any type of information or knowledge that might result in loss of an advantage or level of security if disclosed to others. Loss, misuse, modification or corruption of, or unauthorized access to sensitive information may adversely affect the privacy, reputation, finances or welfare of an individual, and trade secrets, reputation, and finances of a business, depending on the level of sensitivity and nature of the information.

Due to the intangible nature of electronic data, in conjunction with the potential ease of undetected data copying (theft) or corruption, a variety of data protection methods and devices can be employed to protect sensitive data. Data protection methods and devices may be adapted and/or employed to provide a level of data protection suitable to the device containing the data (e.g., memory chip or hard disk drive) or media (e.g., cable or free space) through which the data is transmitted. In certain applications, a combination of data protection methods or devices (e.g., physically securing equipment containing data and encrypting data using an encryption algorithm) may be employed to provide a level of protection greater than the use of a single method or device.

SUMMARY

Various aspects of the present disclosure may be useful for providing a high level of security for digital data contained on an integrated circuit (IC) chip. A security apparatus configured according to embodiments of the present disclosure may prevent discovery of critical IC chip structures and functions by unauthorized personnel or entities.

Embodiments may be directed towards an apparatus for providing security for an integrated circuit (IC) chip configured to contain data. The apparatus may include a printed circuit board (PCB). The PCB may include the IC chip, attached to a surface of the PCB, and a first conformal coating layer that is electrically insulative and attached to at least the surface of the PCB and to exposed surfaces of the IC chip. The PCB may also have a Wheatstone bridge circuit configured to indicate changes to a second conformal coating layer that is X-ray opaque, optically opaque and electrically resistive and attached to the first conformal coating layer. The Wheatstone bridge circuit may include four resistors, each resistor including a region of the second conformal coating layer. The Wheatstone bridge circuit may also include four sets of at least two electrically conductive pads formed on the surface of the PCB, each set of the four sets electrically connected, through openings in the first conformal coating layer, to a corresponding resistor of the four resistors. The Wheatstone bridge circuit may also include a voltage source, electrically connected to at least two pads of the four sets of at least two electrically conductive pads and a monitoring device, electrically connected to another at least two pads of the four sets of at least two electrically conductive pads and configured to detect a change of resistance of the Wheatstone bridge circuit.

Embodiments may also be directed towards a method for fabricating, for an integrated circuit (IC) chip attached to a surface of a printed circuit board (PCB), a security apparatus including a Wheatstone bridge circuit. The method may include creating, on the surface of the PCB, four sets of at least two electrically conductive pads and depositing a first conformal coating layer that is electrically insulative upon at least the surface of the PCB and exposed surfaces of the IC chip. The method may also include creating openings, corresponding to the four sets of at least two electrically conductive pads, in the first conformal coating layer and depositing a second conformal coating layer that is X-ray opaque, optically opaque and electrically resistive onto the first conformal coating layer. The method may also include creating four resistors of the Wheatstone bridge circuit by removing material to divide the second conformal coating layer into four regions.

Embodiments may also be directed towards a method for operating, for an integrated circuit (IC) chip mounted on a surface of a printed circuit board (PCB), a security apparatus including a Wheatstone bridge circuit. The method may include measuring, with a monitoring device and a voltage source, a first resistance value of the Wheatstone bridge circuit and storing the first resistance value. The method may also include measuring, with a monitoring device and a voltage source, a second resistance value of the Wheatstone bridge circuit and determining, by comparing the second resistance value to the first resistance value, a difference between the second resistance value to the first resistance value. The method may also include executing, in response to a difference between the second resistance value of the Wheatstone bridge circuit and the first resistance value of the Wheatstone bridge circuit, a protective action on the IC chip.

Aspects of the various embodiments may be used to provide optical and X-ray shielding of critical structures within an IC chip. Aspects of the various embodiments may also be useful for providing cost-effective security enhancement for use with IC chips attached to printed circuit boards (PCBs) by using existing and proven PCB materials, design and fabrication tools and technologies.

The above summary is not intended to describe each illustrated embodiment or every implementation of the present disclosure.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

Figure 1:
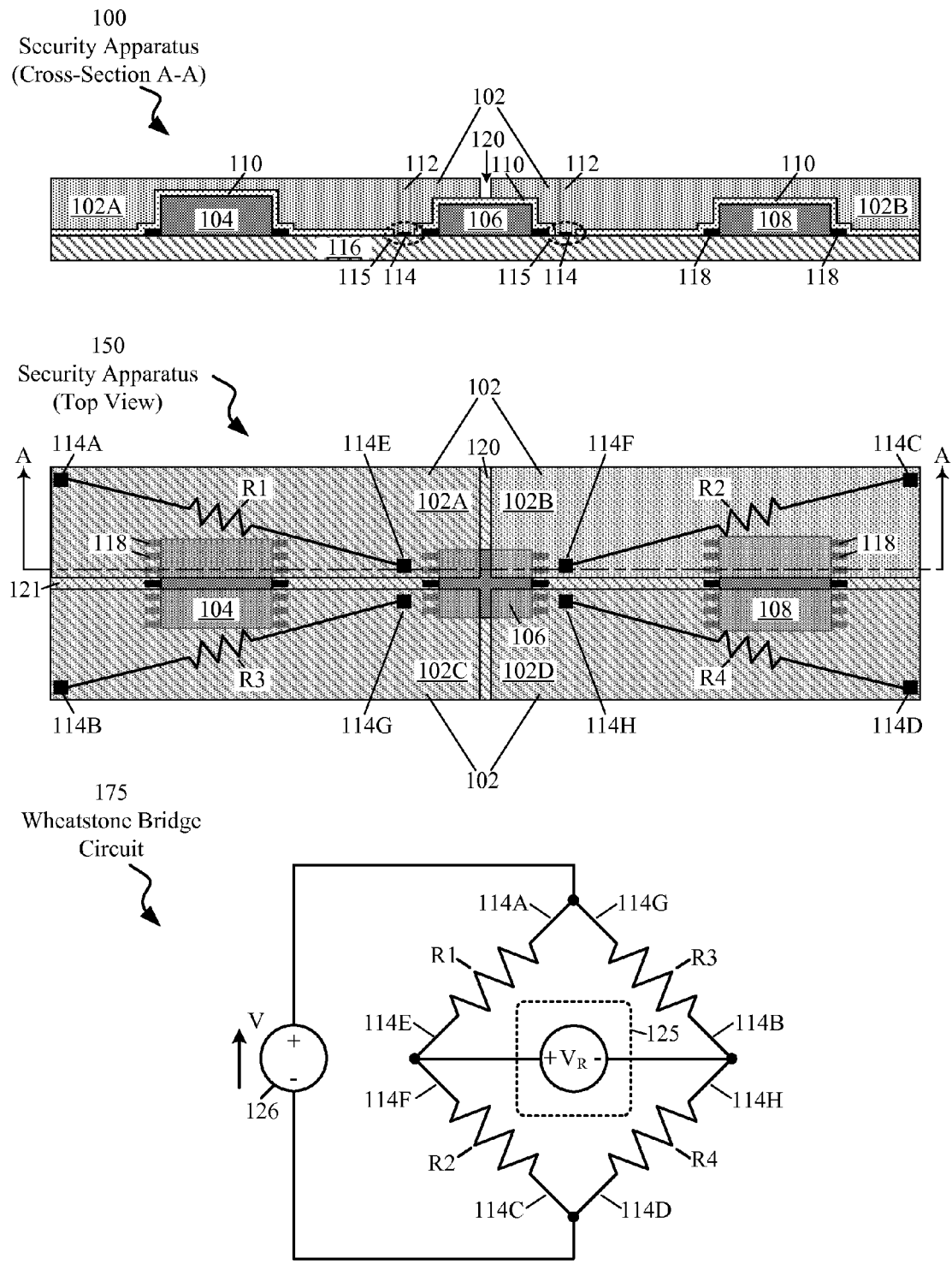
FIG. 1 includes a cross-sectional view and a top view of a security apparatus and a schematic diagram of a Wheatstone bridge circuit included in the security apparatus, according to embodiments of the present disclosure.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

In the drawings and the Detailed Description, like numbers generally refer to like components, parts, steps, and processes.

DETAILED DESCRIPTION

Certain embodiments of the present disclosure can be appreciated in the context of providing enhanced security for digital data contained within integrated circuit (IC) chips that are attached to a printed circuit board (PCB). Such IC chips may be used to store or process sensitive data such as classified, commercial or personal sensitive data. Such classified data may include, but are not limited to strategic targeting information, encryption keys and passwords. Commercial or personal sensitive data may include financial records, information related to commercial or trade secrets, business strategies and advanced product information. While not necessarily limited thereto, embodiments discussed in this context can facilitate an understanding of various aspects of the disclosure. Certain embodiments may also be directed towards other equipment and associated applications, such as rendering one or more particular IC chips tamper-proof, in order to safeguard key operating information and/or chip structure or function. Such IC chips may be used in a wide variety of commercial and consumer electronic devices such as game consoles, computer systems, and mobile devices such as cell phones.

The storage and processing of sensitive digital data by IC chips and electronic systems can be important in commercial, and private sector enterprises. The potential for significant loss of strategic information, financial resources, personal or commercial reputation and business trade secrets resulting from compromised security of sensitive data drives the need for data security devices and measures for IC chips.

A PCB having an IC containing sensitive data may be protected by enclosing the PCB inside a metal (e.g., aluminum) enclosure, and encapsulating the PCB with an opaque material such as polyurethane containing an electrically conductive mesh. A protective device of the sort may provide a measure of security, however, it may also be expensive to fabricate and have multiple yield detractors.

Embodiments of the present disclosure provide a protective device having multiple, integrated levels of data security, while using a low number of materials and corresponding manufacturing process. Embodiments of the present disclosure may provide detection of tampering activity on a PCB, and may be used to alert protective devices to prevent unauthorized access, to data or chip structural information, through erasure, rewriting or destruction of sensitive chip structures and/or data.

Various embodiments of the present disclosure relate to providing multiple levels of enhanced security for digital data stored on an IC chip. Various embodiments may be useful for providing a security device having a relatively low-cost, and that has a simple implementation. Digital data that is represented as stored charge, for example in a dynamic random-access memory (DRAM) device, and data that is represented as electrical interconnection structures (e.g., fuses) may both be protected by the various embodiments of the present disclosure.

According to embodiments, a security apparatus for an IC chip attached to a PCB may provide multiple levels of protection or sensitive data contained within the chip. A security device may be used to shield data within the chip, that is encoded through electrical interconnect structures, from visual and/or X-ray examination. In certain embodiments, a Wheatstone bridge circuit, including four resistors formed from an electrically resistive conformal coating layer deposited onto the IC chip and the PCB may be employed as a tamper sensing device. Data contained within the IC chip may be safeguarded through erasure, scrambling or destruction of the chip, in response to tamper activity detected by changes to the Wheatstone bridge circuit.

Certain embodiments relate to the protection of sensitive data stored on an IC chip, through both passive visible light and X-ray shielding and active detection, through the use of a Wheatstone bridge circuit, of potential tampering activity. FIG. 1 includes a cross-sectional view 100 and a top view 150 of a security apparatus and a schematic diagram 175 of a Wheatstone bridge circuit included in the security apparatus, according to embodiments of the present disclosure. The security apparatus depicted in FIG. 1 may be generally used as a device to provide active and passive protection of sensitive data stored on one or more IC chips (e.g., 104, 106 and 108) mounted on a PCB 116. Sensitive data may be represented (stored) on an IC (e.g., in a dynamic random-access memory or DRAM) chip, by regions of stored charge such as capacitors. In certain embodiments, sensitive data may be represented (stored) on an IC chip by patterns of electrical interconnect structures such as wiring or fuses.

The security apparatus depicted in FIG. 1 is fabricated on a PCB 116 having one or more IC chips (e.g., 104, 106 and 108) attached. PCB 116 may be consistent with a PCB assembly fabricated using established manufacturing processes, materials and techniques. IC chips (e.g., 104, 106 and 108) may have a wide variety of functions, package sizes, and electrical leads types/configurations. For simplicity of illustration, IC chips 104, 106 and 108 are depicted having surface-mount style chip leads 118. Chip leads 118 may include copper, nickel or other electrically conductive materials, and may be electrically connected to conductive structures such as capture pads and/or copper traces on a surface of the PCB 116. Four sets of at least two conductive pads 114A-114H are formed on a surface of the PCB 116, and may be used to electrically interconnect resistors R1-R4 of the Wheatstone bridge circuit 175 to voltage source 126 and monitoring device 125. Vias 112 may be used to form a connection between electrically conductive pads 114A-114H and resistive regions of the second conformal coating layer (e.g., 102A, 102B, 102C, 102D). Resistive regions 102A-102D are electrically isolated from each other by nonconductive areas (gaps) 120, 121. Openings 115 in the first conformal coating layer 110 may be useful to allow second conformal coating layer 102 access to directly contact conductive pads 114A-114H.

First conformal coating layer 110 is an electrically insulative layer deposited on a top surface of both the PCB 116 and exposed surfaces of IC chips 104, 106 and 108. The first conformal coating layer 110 may be useful to provide electrical insulation between the PCB 116 (i.e., exposed conductive capture pads and traces), the chip leads 118 of IC chips 104, 106 and 108 and electrically conductive second conformal coating layer 102.

The second conformal coating layer 102 may be useful for providing optically and X-ray opaque shielding over the PCB 116 and the IC chips 104, 106 and 108. Optical and X-ray opaque shielding may prevent electrical interconnect structures, which may contain encoded data, from being easily observed, for example, using a variety of types of microscopes and/or X-ray imaging equipment. The second conformal coating layer 102 may also be electrically resistive, and therefore useful for creating four resistors (R1-R4) of the Wheatstone bridge circuit 175.

The resistance of, or voltage across the Wheatstone bridge circuit including resistors R1-R4 constructed from regions 102A-102D of second conformal coating layer 102, may vary (from the resistance of an original configuration) in response to tampering with layer 102. Possible examples of tampering of layer 102 may include drilling, cutting, delaminating, grinding, sanding or etching through the use of various chemicals, such as acids or solvents.

Sensing a variation in the resistance of, or voltage across, the Wheatstone bridge circuit may be useful in detecting possible tampering activity, and initiating protective action to ensure that data contained on an IC chip (e.g., 104, 106 and 108) is secured. Voltage source 126 may be used to apply a voltage (V) to the Wheatstone bridge circuit 175, and monitoring device 125 may be used to measure a resulting voltage ($V_R$) across the circuit 175.

The initial bulk resistivity of the second conformal coating layer 102 may not need to be held in a particular range during manufacturing (i.e., a variety of initial resistances is possible), as a change of the Wheatstone bridge circuit resistance (sensed as a change of voltage $V_R$) will inform a monitoring device that a tamper event has occurred. In certain embodiments, multiple Wheatstone bridge circuits 175 may be useful in order to increase PCB and IC chip coverage area and/or sensitivity over the use of a single Wheatstone bridge circuit.

In particular embodiments, an electrically insulative coating may be deposited onto the second conformal coating layer 102, which may be useful in preventing accidental false-positive "tamper detections" due to handling of the PCB 116, or from contact with a conductive or electrostatically charged item.

For ease of discussion, the term "resistance measurement" is used herein, with respect to measurement(s) performed on a Wheatstone bridge circuit (view 175, FIG. 1). It may be understood, however, that a "resistance" measurement may involve obtaining a voltage $V_R$ across the Wheatstone bridge circuit using a monitoring device and a voltage source (e.g., 125, 126, respectively, FIG. 1). A voltage $V_R$ may be a useful indicator of a change of resistance of at least one of the resistors (e.g., R1-R4, FIG. 1) of a Wheatstone bridge circuit.

Figure 2:
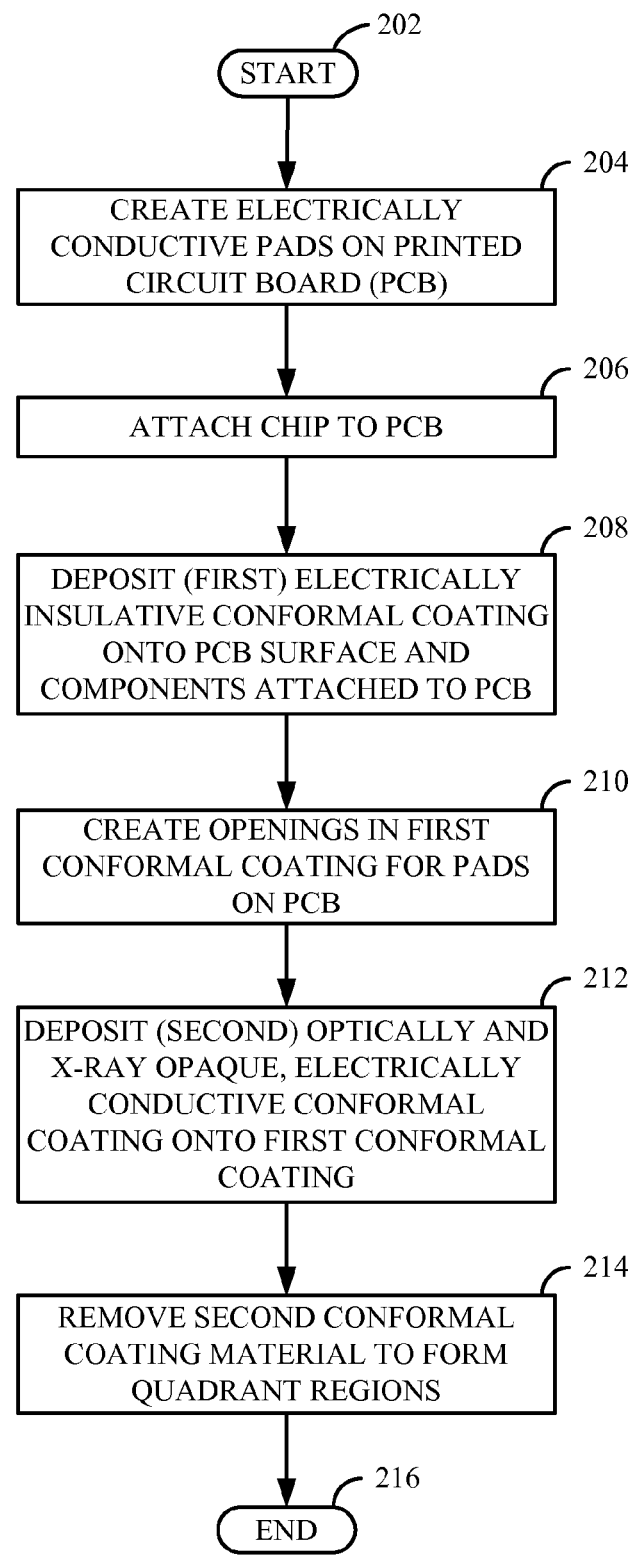
FIG. 2 is a flow diagram illustrating steps for fabricating a security apparatus, according to embodiments consistent with the figures.

FIG. 2 is a flow diagram illustrating a method for fabricating a security apparatus, according to embodiments consistent with the figures. The method for fabricating a security apparatus 200 can be useful for creating a protective structure, for an IC chip and a PCB, that is both X-ray and optically opaque and that is compatible with existing PCB material sets and fabrication technologies. Operations discussed in reference to FIG. 2 may generally correspond to the results of process operations depicted in FIG. 3. The process 200 moves from start 202 to operation 204.

Operation 204 generally refers to the process steps that involve creating four sets of at least two electrically conductive pads (e.g., 114, FIG. 3) on the surface of the PCB (e.g., 116, FIG. 3), which corresponds to view 301 (FIG. 3) and its associated description. The four sets of at least two electrically conductive pads (e.g., 114A-114H, FIG. 1) may be useful in electrically connecting a voltage source (e.g., 126, FIG. 1) and a monitoring device (e.g., 125, FIG. 1) to resistors (e.g., R1-R4, FIG. 1) of a Wheatstone bridge circuit.

In certain embodiments, additional sets of electrically conductive pads may be created on the surface of the PCB to electrically connect at least one additional voltage source and at least one monitoring device to at least one additional Wheatstone bridge circuits. Fabricating and using multiple Wheatstone bridge circuits may have certain benefits, such as increased protection sensitivity over certain regions of an IC chip and/or PCB surface. Once conductive pads have been created on the surface of the PCB, the process moves to operation 206.

Operation 206 generally refers to the process steps that involve attaching at least one chip (e.g., 104, 106, 108, FIG. 3) to the surface of the PCB (e.g., 116, FIG. 3), which corresponds to view 301 (FIG. 3) and its associated description. At least one of the chips (e.g., 104, 106, 108, FIG. 3) may be configured to contain sensitive data, and chips may include electrically conductive leads (e.g., 118, FIG. 3) that remain exposed after the chip is attached to the PCB. Once at least one chip has been attached to the PCB, the process moves to operation 208.

Figure 3:
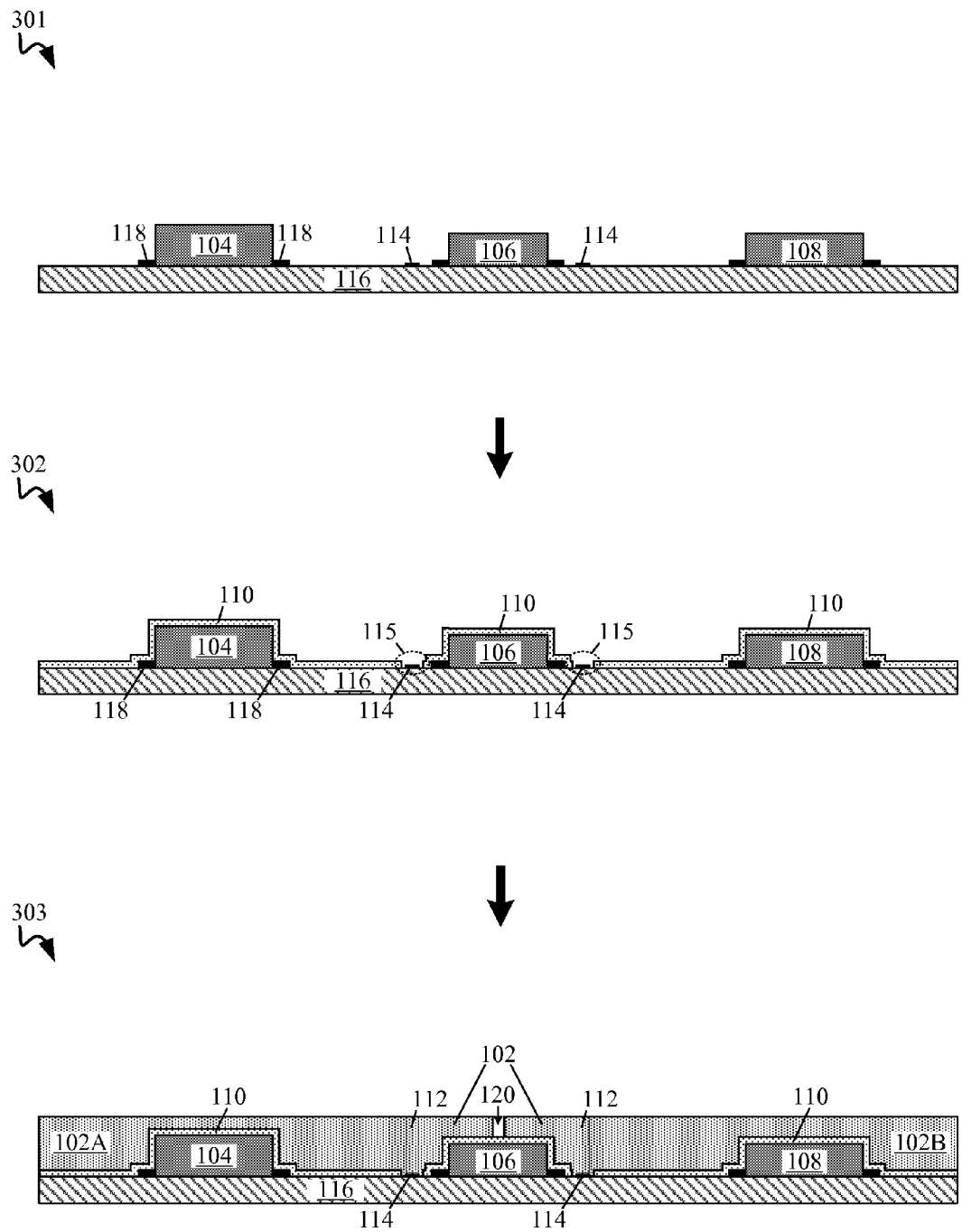
FIG. 3 includes three cross-sectional views illustrating the results of process steps for fabricating a security apparatus, according to embodiments consistent with the figures.

Operation 208 generally refers to the process steps that involve depositing a first, electrically insulative conformal coating layer onto at least the surface of the PCB (e.g., 116, FIG. 3) and exposed surfaces of the IC chip (e.g., 104, 106, 108, FIG. 3), which corresponds to view 302 (FIG. 3). The first conformal coating layer (e.g., 110, FIG. 3) can provide an electrically insulative layer between electrically conductive leads (e.g., 118, FIG. 3) and subsequent layers deposited onto the first conformal coating layer. Prior to the deposition process, openings 115 may be masked, using a photomask/photolithography process.

In certain embodiments, depositing a first, electrically insulative conformal coating layer may also include depositing the coating onto at least one other surface of the PCB, for example at least one of the sides and/or the surface of the PCB opposite of the surface the IC chip is mounted to. Once electrically insulative conformal coating layer has been deposited onto the PCB and the chip, the process moves to operation 210.

Operation 210 generally refers to the process steps that involve creating openings (e.g., 115, FIG. 3), corresponding to the four sets of at least two electrically conductive pads, in the first conformal coating layer, which corresponds to view 302 (FIG. 3). Openings may be created in the first conformal coating layer 110 (FIG. 3) through the removal of a mask layer (deposited in operation 208) or through a separate process including photomasking and etching, to remove areas of the first conformal coating layer 110 (FIG. 3). Openings 115 in the first conformal coating layer can be useful in providing access to the four sets of at least two electrically conductive pads on the PCB (e.g., 114, FIG. 3), to establish electrical contact between the pads and a subsequent deposited layer. Once electrically insulative conformal coating layer has been deposited onto the PCB and the chip, the process moves to operation 212.

Operation 212 generally refers to the process steps that involve depositing a second, electrically conductive conformal coating layer (e.g., 102, FIG. 1) onto the first conformal coating layer (e.g., 110, FIG. 3), which corresponds to view 303 (FIG. 3). The second conformal coating layer may be X-ray opaque, optically opaque and electrically resistive, which may be useful for absorbing (blocking) X-ray radiation and visible light from the PCB 116 (FIG. 3) and each the chips 104, 106, 108 (FIG. 3). Blocking x-ray radiation and visible light may hinder or prevent discovery of physical structures and/or contents of one or more of the chips and/or PCB. The resistive property of the second conformal coating layer may be useful in creating resistors of the Wheatstone bridge circuit (view 175, FIG. 1).

In certain embodiments, depositing a second conformal coating layer (e.g., 102A, 102B, FIG. 3) can include depositing the coating onto the first conformal coating layer (e.g., 110, FIG. 3) that is deposited onto at least one other surface of the PCB, for example one or more sides and/or a surface opposite to the surface the IC chip is mounted on. Depositing the second conformal coating layer upon additional surfaces may be useful in the creation of additional sets of resistors for additional Wheatstone bridge circuits, which may cover the greater portion of the PCB total surface area. Additional deposition of the second conformal coating layer may also provide optical and x-ray shielding for a greater portion of the PCB total surface area. Once electrically insulative conformal coating layer has been deposited onto the PCB and the chip, the process moves to operation 214.

Operation 214 generally refers to the process steps that involve creating four resistors of the Wheatstone bridge circuit (view 175, FIG. 1) by removing material to divide the second conformal coating layer into four resistive regions (e.g., 102A, 102B, 102C, 102D, FIG. 1), which corresponds to view 303 (FIG. 3). The four resistors of the Wheatstone bridge circuit (view 175, FIG. 1) are electrically contacted by the electrically conductive pads (114, FIG. 3, 114A-114H, FIG. 1) adjoining the four regions (e.g., 102A, 102B, 102C, 102D, FIG. 1) of the second conformal coating layer. The resistivity of the second conformal coating layer may be specified through the material composition and/or dimensions (e.g., thickness) of the second conformal coating layer.

In certain embodiments, the second conformal coating layer may be divided into multiple sets of four resistors, corresponding to multiple Wheatstone bridge circuits, which may be useful for providing increased coverage of IC chips on the PC board. For example, a second set of four resistors on a second side of the PC board may be useful for adding additional shielding from optical light and x-rays, as well as providing an indicator of possible tampering activity on the PCB. Once the four Wheatstone bridge circuit resistors are created by removing material from the second conformal coating layer, the process 200 may end at block 216.

FIG. 3 includes a set of three cross-sectional views 301-303 depicting the results of a sequential set of process steps for fabricating a security apparatus, according to embodiments consistent with the figures. The views 301-303 may be useful in illustrating details involved in fabricating a security apparatus for an (IC) chip attached to a surface of a PCB. The security apparatus can include optical and X-ray shielding and provide a Wheatstone bridge circuit which can be used to detect tampering activity on the PCB. PCB 116 may be fabricated using a variety of different PCB fabrication processes that can be selected based upon the particular application.

View 301 depicts a PCB 116 having electrically conductive pads 114 formed on a surface, and IC chips 104, 106 and 108 mounted to the same surface. PCB 116 may be consistent with a variety of different printed circuit boards fabricating processes and materials. For example, PCB 116 may be a multi-layer structure including alternating layers of a dielectric material (e.g., epoxy resin) and a conductive material (e.g., copper). In embodiments, PCB 116 includes four sets of at least two electrically conductive pads 114, formed on a surface of the PCB 116. Electrically conductive pads 114 may include metals such as copper or nickel. Electrically conductive structures (e.g., wires and vias) may be included in PCB 116 to connect electrically conductive pads 114 to a voltage source (e.g., 126, FIG. 1) and to a monitoring device (e.g., 125, FIG. 1). In embodiments, the size and position of electrically conductive pads 114 may be specified to be appropriate for electrical connection to resistors (e.g., R1-R4, FIG. 1) for a Wheatstone bridge circuit (view 175, FIG. 1). In certain embodiments, IC chips 104, 106 and 108 may be mounted to PCB 116 using a process such as solder reflow or wave soldering.

View 302 depicts the results of the deposition of a first conformal coating layer 110 upon a surface of the PCB 116 and upon exposed surfaces of IC chips 104, 106 and 108. The first conformal coating layer 110 may be useful as a dielectric barrier, to electrically insulate exposed chip leads (e.g., 118) and other exposed conductors, such as wiring traces and connection pads, on a surface of a PCB. In embodiments, a masking/photomasking process may be used to create openings 115, corresponding to the four sets of at least two electrically conductive pads 114, in the first conformal coating layer 110. Openings 115 may be useful to allow subsequent layers (e.g., an electrically resistive layer) to selectively contact electrically conductive pads 114, while still allowing the first conformal coating layer 110 to insulate the remainder of a PCB surface and IC chip exposed surfaces. In certain embodiments, the first conformal coating layer may include a polymer such as parylene, which may be deposited using a chemical-vapor deposition process, in a vacuum chamber. The first conformal coating layer may also include Dow Corning silicone products such as Sylgard® encapsulants. In particular embodiments, the first conformal coating layer may be deposited upon additional surfaces, which can include at least one side and/or planar surface of PCB, which may be useful for providing more complete insulation of the PCB and/or IC chips, and for providing a surface upon which to deposit subsequent conformal coating layers.

View 303 depicts the results of the deposition of a second conformal coating layer 102 onto a surface of the first conformal coating layer 110 and upon exposed surfaces of IC chips 104, 106 and 108. Second conformal coating layer 102 may be electrically resistive, and can be useful in creating four resistors (e.g., R1-R4) of the Wheatstone bridge circuit (view 175 FIG. 1). Second conformal coating layer 102 may also be useful in shielding both IC chips (e.g., 106) and the PCB 116 from exposure to visible light and X-ray radiation, which may inhibit detection of data containing structures that are included within the PCB or the IC chip.

In certain embodiments, the second conformal coating layer 102 may include an electrically conductive polymer such as polyaniline (PANI). Polyaniline may be deposited onto the first conformal coating layer 110 through processes such as electrodeposition, or pouring of polyaniline, in a liquid state, into a mold created to fit the PCB 116. In certain embodiments, polyaniline may be doped with conductive materials such as metal flakes, powder or spheres to increase its electrical conductivity. In certain embodiments, the conductivity of polyaniline may be in a range between $10^{-5}$ and $10^{-6}$ Siemens per centimeter (S/cm).

According to embodiments, the second conformal coating layer 102 may be divided, by the removal of portions of the coating material to create gaps (e.g., 120) between sections of the material, resulting in the creation of four resistors of the Wheatstone bridge circuit (view 175, FIG. 1). In certain embodiments, portions of the second conformal coating layer 102 may be removed through processes including laser ablation or a physical cutting, for example using a saw or other abrasive device. In particular embodiments, second conformal coating layer material 102 may be removed through the use of photolithographic etching techniques.

In certain embodiments, the second conformal coating layer 102 may be portioned into separate regions through a molding process. In certain embodiments, the four resistors formed by material removal or molding may have similar areas, which may produce four resistors (e.g., R1-R4, FIG. 1) having approximately similar resistance values.

According to embodiments, depositing a second conformal coating layer 102 may include depositing the coating onto the first conformal coating layer 110 that has been deposited onto at least one other surface of the PCB. For example, the second conformal coating layer 102 may be deposited onto the first conformal coating layer 110 on both planar surfaces of a PCB, which may result in greater optical light and X-ray shielding and an increased area for creation of resistors for a Wheatstone bridge temper-detection circuit.

In embodiments, vias 112 may be created within the second conformal coating layer 102 that are an electrical contact with electrically conductive pads 114. Vias 112 may be useful in establishing a more robust electrical connection to the second conformal coating layer 102 and may be possible using electrically conductive pads 114 alone. Vias 112 may also be useful, if placed around a periphery of second conformal coating layer 102, in providing electromagnetic shielding for the PCB 116 and IC chips 104, 106 and 108.

In certain embodiments, the second conformal coating layer 102 may be deposited over an entire surface of a PCB 116. In particular embodiments, the second conformal coating layer 102 may be deposited over multiple surfaces of a PCB 116, for example, over two planar surfaces and one or more sides of the PCB 116.

In certain embodiments, the second conformal coating layer 102 may include a material such as barium sulfate, which may be useful in absorbing X-ray radiation, and preventing X-ray based analysis of the PCB 116 and/or IC chips 104, 106 and 108. Certain embodiments may include a third, electrically nonconductive, conformal layer deposited onto the second conformal coating layer 102. A third, nonconductive layer may be useful in electrically insulating the second conformal coating layer 102, and in associated Wheatstone bridge circuit (view 175, FIG. 1) from electrical disruption (an unintentional "false positive" detection of tampering activity) due to handling and/or contact of the resistors to conductive materials. Barium sulfate may be also be added, in embodiments, to the third, nonconductive layer to enhance X-ray absorption. In particular embodiments, a fourth, nonconductive, X-ray inhibiting layer containing barium sulfate may be added between the second conformal coating layer 102 and the third, nonconductive/protective layer. The variations of conductive/nonconductive and X-ray absorptive layer structures described herein are not limiting, and may be used in various combinations.

Figure 4:
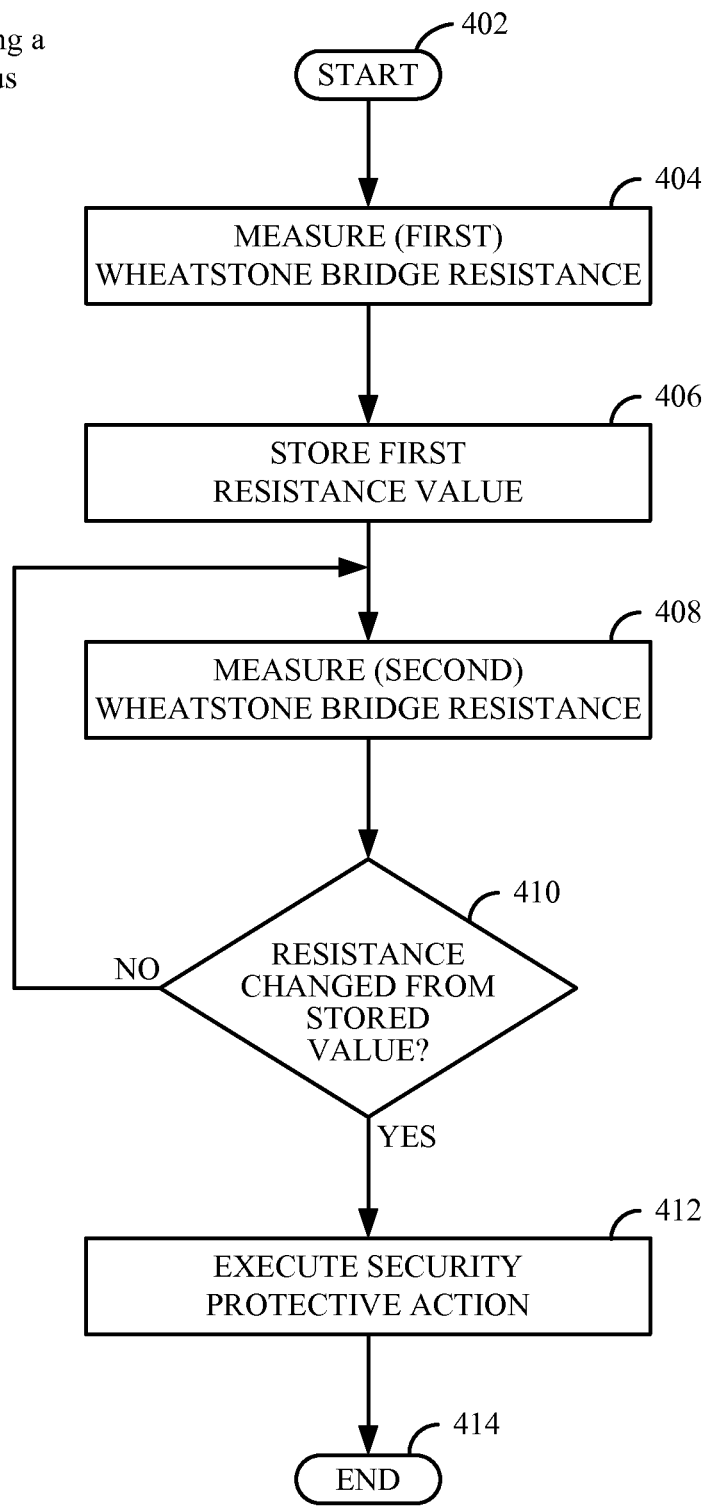
FIG. 4 is a flow diagram illustrating steps for operating a security apparatus, according to embodiments consistent with the figures.

FIG. 4 is a flow diagram illustrating a method for operating a security apparatus, including a Wheatstone bridge circuit (view 175, FIG. 1) according to embodiments consistent with the description and figures herein. The method for operating a security apparatus 400 can be useful for detecting a tampering event, related to an IC chip (e.g., 106, FIG. 1) and/or a PCB (116, FIG. 1), which may be intended to reveal sensitive contents of the IC or the PCB. For example, a tampering event, if successful, may reveal to an unauthorized user or entity, sensitive data encoded within interconnect structures on IC chip (e.g., 106, FIG. 1). The method for operating a security apparatus 400 may also be useful in initiating, in response to a detected tampering event, a protective action designed to safeguard sensitive data included on an IC chip (e.g., 106, FIG. 1) and/or a PCB (116, FIG. 1). The active detection of, and response to, a tampering event described in reference to FIG. 4 is supplemented by the (passive) protection, described herein, provided by the optically and X-ray opaque second conformal coating layer 102. The process 400 moves from start 402 to operation 404.

Operation 404 generally refers to measuring, through the use of a monitoring device (125, FIG. 1) and a voltage source (126, FIG. 1), a first resistance value of the Wheatstone bridge circuit (view 175, FIG. 1). The first resistance measurement may be a measurement of the Wheatstone bridge circuit (view 175, FIG. 1) resistance in an initial state, for example, upon the power-up of a system, or after completion of manufacturing of the PCB (116 FIG. 1). The first resistance measurement may be used as a reference measurement, from which to determine changes in resistance of the Wheatstone bridge circuit (view 175, FIG. 1). Wheatstone bridge circuit resistance changes can indicate that tampering, such as partial removal of the second conformal coating layer (102, FIG. 1), through etching, grinding, peeling or other means, has occurred.

A monitoring device (e.g., 125 FIG. 1) may include, for example, a voltage measurement circuit, designed to measure a voltage determined by a voltage source (e.g., 126, FIG. 1) and a ratio of resistances of resistors (R1-R4, FIG. 1) used in constructing the Wheatstone bridge circuit (view 175, FIG. 1). A change of resistance of any one or a combination of the resistors of the Wheatstone bridge circuit may result in a change of voltage $V_R$ (FIG. 1). In certain embodiments, the monitoring device (e.g., 125 FIG. 1) may be located on an IC chip (e.g., 106, FIG. 1) configured to contain sensitive data. In certain embodiments, the monitoring device (e.g., 125 FIG. 1) may be located on another IC chip, on the PCB (116, FIG. 1), or in a remote location. Once the first resistance value of the Wheatstone bridge circuit has been measured, the process moves to operation 406.

Operation 406 generally refers to storing the first resistance value, measured in operation 404, of the Wheatstone bridge circuit. The first resistance measurement may be in the form of a numerical value, which may be stored in a non-volatile memory device such as a flash memory, or burned into e-fuses, for later retrieval and use. In certain embodiments, the first resistance value may be stored on a chip configured to contain sensitive data. In particular embodiments, the first resistance value may be stored on another chip or in another location. In embodiments including multiple Wheatstone bridge circuits (view 175, FIG. 1), a first resistance value may be stored for each respective Wheatstone bridge circuit. Once the first resistance value of the Wheatstone bridge circuit has been stored, the process moves to operation 408.

Operation 408 generally refers to measuring, through the use of a monitoring device (125, FIG. 1) and a voltage source (126, FIG. 1), a second resistance value of the Wheatstone bridge circuit (view 175, FIG. 1). The second (and subsequent) resistance measurements may be a measurement(s) of the Wheatstone bridge circuit (view 175, FIG. 1) resistance at some point(s) in time following the power-up of a system or completion of manufacturing of the PCB (116 FIG. 1). Second and subsequent Wheatstone bridge circuit resistance measurements may be made on a continual or periodic basis, depending on a particular level of security for a given PCB and/or sensitive IC chip. Once the second resistance value of the Wheatstone bridge circuit has been measured, the process moves to decision 410

At operation 410 a decision is made regarding a difference between the first resistance measurement of the Wheatstone bridge circuit (taken in operation 404 and stored in operation 406) and second and subsequent Wheatstone bridge circuit resistance measurements (taken in operation 408). A change of resistance of the Wheatstone bridge circuit (view 175, FIG. 1) may indicate a change in at least one of the resistors R1-R4 of the circuit, which may indicate some form of tampering activity, such as an attempt to remove at least part of the second conformal coating layer 102 from the PCB 116 (FIG. 1).

In general, the voltage $V_R$ measured by a monitoring device 125 (FIG. 1) of a Wheatstone bridge circuit including four resistors R1-R4 (view 175, FIG. 1) may be determined in accordance with the following equation:

$$V_R = V * ((R_2/(R_1+R_2)) - (R_4/(R_3+R_4)))$$

Where:
$R_1$=resistance of resistor R1
$R_2$=resistance of resistor R2
$R_3$=resistance of resistor R3
$R_4$=resistance of resistor R4
V=the voltage supplied by voltage source 126 (FIG. 1)

In general, the second conformal coating layer regions (102A-102D, FIG. 1) may be designed and fabricated such that the resistors R1-R4 (view 175, FIG. 1) have approximately equal resistance values, which may yield a (first or initial) voltage $V_R$ measurement (see operation 404) of approximately 0 Volts (V). However, the fabrication process (operation 212, FIG. 2) used to create the resistors R1-R4 may yield resistors with resistance values that may vary from each other, causing the first or initial voltage $V_R$ measurement to vary from approximately 0 Volts (V). For example, according to the above equation, if resistors R1, R3 and R4 each have a value of 50 Ohms (Ω) and resistor R2 has a value of 55Ω, then the resulting measured value of $V_R$ may be 23.8 mV. In this example, the (initial) value of 23.8 mV may be stored, per operation 406. Second and subsequent measurements (operation 408) may be compared against this initial measurement, which may have the effect of "zeroing out" (compensating for) any initial $V_R$ offset from 0 V that is due to manufacturing variations.

Measurements of voltage $V_R$ may change slightly over time in response to a number of causes. For example, monitoring device 125 (FIG. 1) may produce slightly different measurements due to environmental factors such as supply voltage/voltage variation and temperature. Resistors R1-R4 (view 175, FIG. 1) may undergo slight changes in resistance values, over time, due to factors such as material changes/degradation, or changes in an interface between the second conformal coating layer (102, FIG. 1) and electrically conductive pads (114, FIG. 1).

In order to prevent the above variations in voltage $V_R$ measurements from producing "false positive" indications of tampering activity of the second conformal coating layer (102, FIG. 1), a tolerance value may be used in the determination of a difference between a stored $V_R$ measurement and a second/subsequent $V_R$ measurement. The tolerance value may be determined through calculations and/or electrical/material simulations to account for a variety of expected variations of $V_R$ measurements due to effects that are not related to tampering activity, as described above. For example, a tolerance value of +/−30 mV may be employed in the comparison between a stored $V_R$ measurement and a second/subsequent $V_R$ measurement. Thus, following the example, if a second/subsequent $V_R$ measurement varies from a stored $V_R$ measurement by more than 30 mV (either greater than or less than the stored $V_R$ measurement value), then the $V_R$ measurement will be determined to have changed from the stored $V_R$ measurement value. If however, the second/subsequent $V_R$ measurement does not vary from a stored $V_R$ measurement by more than 30 mV, then the $V_R$ measurement will be determined to have not changed from the stored $V_R$ measurement value.

The determination of a $V_R$ measurement tolerance value may take into account the above-mentioned factors in conjunction with other factors such as changes in resistance (resulting in changes of $V_R$ measurements) resulting from various types and severities of tampering activity.

The amount of tampering (e.g., the size of a hole drilled in the second conformal coating layer (102, FIG. 1) required to jeopardize the security of data stored on an IC chip (e.g., 106, FIG. 1)) may be considered in order to determine a suitable $V_R$ measurement tolerance value that does not produce false positives and yet still provides effective detection of a variety of types of tampering activity.

In certain embodiments, the $V_R$ measurement tolerance value may be stored on an IC chip (e.g., 106, FIG. 1) containing sensitive data. In some embodiments, the $V_R$ measurement tolerance value may be stored on another IC chip, or in a remote location.

If the second or subsequent resistance measurement has changed by more than a tolerance amount from the first resistance measurement of the Wheatstone bridge circuit, the process moves to operation 412. If the second or subsequent resistance measurement has not changed by more than a tolerance amount from the first resistance measurement, the process returns to operation 408.

Operation 412 generally refers to executing a protective action designed to safeguard sensitive data, contained within an IC chip (e.g., 106, FIG. 1) and/or a PCB (e.g., 116, FIG. 1), from being discovered or revealed. In certain embodiments, protective action may include erasing or erasing, rewriting, or encoding/scrambling data (e.g., data stored in flash or non-volatile memory) from an IC chip. In particular embodiments, a protective action may include destroying a chip structure and/or function (of sensitive or key circuit elements) by, for example, overheating the chip through initiating power dissipation sufficient to cause damage from excess heat. Once the protective action has been taken, the process 400 may end at block 414.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

What is claimed is:
1. An apparatus for providing security for an integrated circuit (IC) chip configured to contain data, the apparatus comprising:
 a printed circuit board (PCB) having:
  the IC chip attached to a surface of the PCB;
  a first conformal coating layer that is electrically insulative and attached to at least the surface of the PCB and to the IC chip;
  a Wheatstone bridge circuit configured to indicate changes to a second conformal coating layer that is X-ray opaque, optically opaque and electrically resistive and attached to the first conformal coating layer, the Wheatstone bridge circuit including:

four regions of the second conformal coating layer that are each configured as corresponding resistor in the Wheatstone bridge circuit;

four sets of at least two electrically conductive pads formed on the surface of the PCB, each set of the four sets electrically connected, through openings in the first conformal coating layer, to a corresponding resistor of the resistors in the Wheatstone bridge circuit;

a voltage source, electrically connected to at least two pads of the four sets of at least two electrically conductive pads; and a monitoring device, electrically connected to another at least two pads of the four sets of at least two electrically conductive pads and configured to detect a change of resistance of the Wheatstone bridge circuit.

2. The apparatus of claim 1, wherein the IC chip is configured to contain data represented by stored charge.

3. The apparatus of claim 1, wherein the IC chip is configured to contain data represented by electrical interconnect structures.

4. The apparatus of claim 1, further comprising a second Wheatstone bridge circuit configured to indicate, in conjunction with another monitoring device, changes to another set of four resistors, each resistor of the another set of four resistors formed from a respective region of the second conformal coating layer.

5. The apparatus of claim 1, further comprising a third conformal coating layer that is electrically insulative and attached to the second conformal coating layer.

6. The apparatus of claim 5, wherein the third conformal coating layer includes barium sulfate.

7. The apparatus of claim 5, further comprising a fourth conformal coating layer, including barium sulfate, deposited between the second conformal coating layer and the third conformal coating layer.

* * * * *